US00PP31914P2

(12) United States Plant Patent
Dannaher et al.

(10) Patent No.: US PP31,914 P2
(45) Date of Patent: Jun. 30, 2020

(54) ***ULMUS* PLANT NAMED 'DAVESSTRAIGHTUP'**

(50) Latin Name: *Ulmus parvifolia*
Varietal Denomination: DavesStraightUp

(71) Applicants: David J Dannaher, Galena, OH (US); Leslie J Dannaher, Galena, OH (US)

(72) Inventors: David J Dannaher, Galena, OH (US); Leslie J Dannaher, Galena, OH (US)

( * ) Notice: Subject to any disclaimer, the term of this patent is extended or adjusted under 35 U.S.C. 154(b) by 0 days.

(21) Appl. No.: 16/502,000

(22) Filed: Jul. 18, 2019

(51) Int. Cl.
*A01H 5/00* (2018.01)
*A01H 6/00* (2018.01)

(52) U.S. Cl.
USPC ..... Plt./221

(58) Field of Classification Search
USPC ..... Plt./221, 226
See application file for complete search history.

*Primary Examiner* — Susan McCormick Ewoldt
(74) *Attorney, Agent, or Firm* — Penny J. Aguirre

(57) ABSTRACT

A new cultivar of *Ulmus* tree named 'DavesStraightUp' that is characterized by its upright and very columnar plant habit, its small leaves, its branch tips that are upright and do not splay with age, its strong crotch angles that are tight and average between 20° and 25° to vertical, its exfoliating bark that tends to curl in strips and reveals colorful patches of orange-tan, grey and white, its fall foliage that turns to yellow and yellow-orange in color and lasts late into the season, and its resistance to Dutch elm disease and phloem neurosis.

2 Drawing Sheets

Botanical classification: *Ulmus parvifolia.*
Variety denomination: 'DavesStraightUp'.

BACKGROUND OF THE INVENTION

The present invention relates to a new and distinct cultivar of *Ulmus parvifolia*, and will be referred to hereafter by its cultivar name, 'DavesStraightUp'. 'DavesStraightUp' is a new cultivar of Chinese elm, a deciduous tree grown for use as a landscape plant.

The new *Ulmus* was discovered as a chance seedling from seeds sown of unnamed plants of *Ulmus parvifolia* in Galena, Ohio in 2001.

Asexual propagation of the new cultivar was first accomplished by grafting in 2010 by the Inventor in Galena, Ohio. Asexual propagation by grafting and budding has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'DavesStraightUp' as a unique cultivar of *Ulmus.*

1. 'DavesStraightUp' exhibits an upright and very columnar plant habit.
2. 'DavesStraightUp' exhibits small leaves.
3. 'DavesStraightUp' exhibits branch tips that are upright and do not splay with age.
4. 'DavesStraightUp' exhibits strong crotch angles that are tight and average between 20° and 25° to vertical.
5. 'DavesStraightUp' exhibits exfoliating bark that tends to curl in strips and reveals colorful patches of orange-tan, grey and white.

6. 'DavesStraightUp' exhibits fall foliage that turns to yellow and yellow-orange in color and lasts late into the season.
7. 'DavesStraightUp' exhibits resistance to Dutch elm disease and phloem neurosis.

Typical plants of the parent species differs from 'DavesStraightUp' in having a wider canopy spread, vase shaped plant habit, fall color that ranges from dull brown to bright red, variable bark exfoliation and leaves that are larger in size. 'DavesStraightUp' can be most closely compared to the *Ulmus parvifolia* cultivars 'BSNUPF' (U.S. Plant Pat. No. 17,655) and 'Emer II' (U.S. Plant Pat. No. 7,552). 'BSNUPF' is similar to 'DavesStraightUp' in having a narrow plant habit when young, dark green leaves that are smaller in size and patches of color when bark exfoliates. 'BSNUPF' differs from 'DavesStraightUp' in having a plant habit that broadens and does not retain a tight columnar plant habit, branch tips that splay outwards and leaves that are larger in size. 'Emer II' is similar to 'DavesStraightUp' in having an upright plant habit and exfoliating bark. 'Emer II' differs from 'DavesStraightUp' in having a vase-shaped habit with arching branches and a larger plant size.

BRIEF DESCRIPTION OF THE DRAWINGS

The accompanying colored photographs illustrate the overall appearance and distinct characteristics of the new *Ulmus*. The photographs were taken of an 18-year-old tree of 'DavesStraightUp' as grown outdoors in a trial bed in Galena, Ohio.

Figure 1:
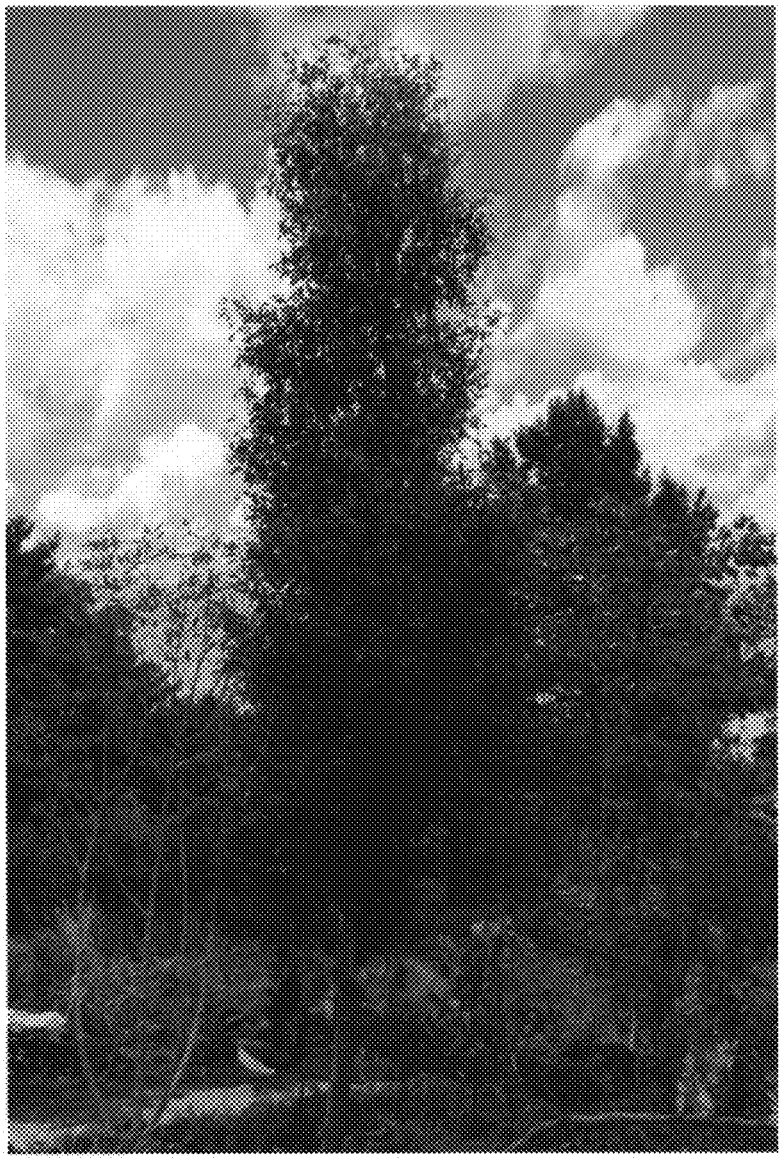
FIG. 1 illustrates the plant habit of 'DavesStraightUp'.
Figure 2:
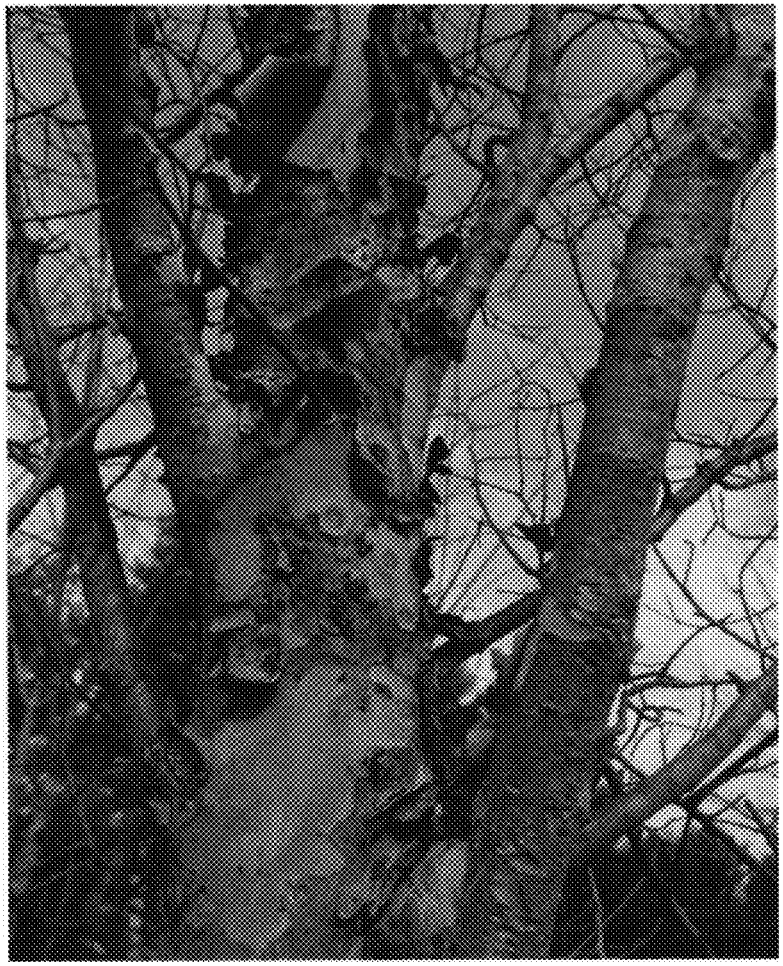
FIG. 2 provides a view of the narrow branch angles and the exfoliating bark of 'DavesStraightUp'.
Figure 3:
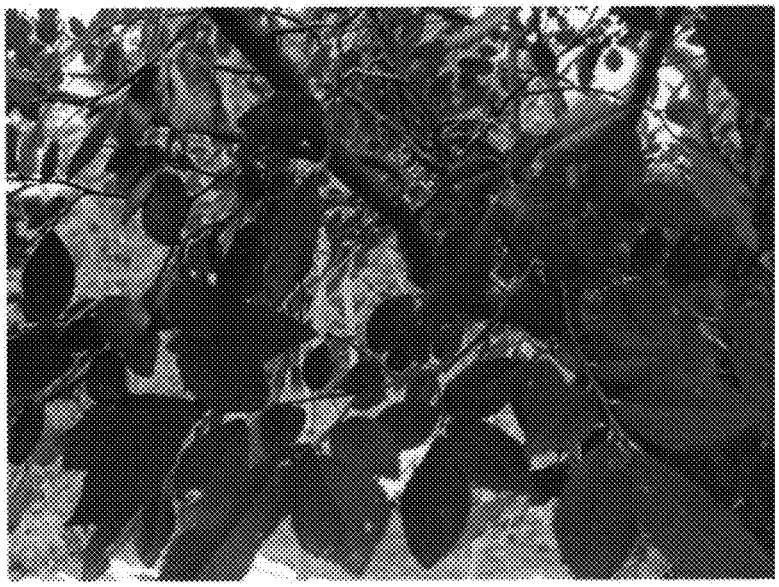
FIG. 3 provides a close-up view of the foliage of 'DavesStraightUp'.

The colors in the photographs may differ slightly from the color values cited in the detailed botanical description, which accurately describe the colors of the new *Ulmus*.

DETAILED BOTANICAL DESCRIPTION

The following is a detailed description of 3-year-old tree of 'DavesStraightUp' as grown outdoors in a 3-gallon container in Galena, Ohio with mature bark and size described from an 18-year-old tree grown outdoors in a trial plot in Galena, Ohio. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Tree habit.*—Deciduous, upright tree with a very columnar habit.

*Height and spread.*—Reaches about 7.62 m in height and about 1.22 m in width as an 18-year-old tree in the landscape.

*Cold hardiness.*—At least to U.S.D.A. Zones 5 to 9.

*Diseases and pests.*—No pest problems have been observed, observed and tested to be resistant to Dutch elm disease (caused by *Ascomycota* sp.) and phloem necrosis also known as elm yellows (caused by phytoplasmas).

*Environmental conditions.*—Tolerant to a variety of environmental conditions including wind, ice, snow load, flooding rainfalls and drought.

*Root description.*—Fibrous, freely branched, 161C in color.

*Propagation.*—Grafting and budding.

*Root development.*—A graft is complete in about 6 months and a young plant from a graft can be obtained in about 18 months.

*Growth rate.*—Moderate, about 61 cm per year.

Branch description:

*Branch shape.*—Slightly oval.

*Branch color.*—Young growth; 144B in color, maturing branches; main trunk 147A, lateral and secondary branches a blend of 147A and 200C, with lenticels; average of 1.5 mm in length, about 10 per square centimeter, 165C in color, mature bark; N201A, when exfoliating; 201A with surface exposed and back of curled bark a blend of 164A, 164B, 156A and N201A.

*Branching.*—About 15 lateral branches with internode length between lateral branches an average of 10 cm, lateral branches held at 20° and 25° angle to vertical.

*Branch size.*—Main trunk; an average of 1.6 m in length and 8 mm in diameter (measured 15 cm from base), lateral branches; up to 30 cm in length and an average of 2 mm in diameter, and secondary branches; an average of 13 cm in length and 1.5 mm in diameter.

*Branch and trunk surface.*—Young growth; smooth and glabrous, mature branches; smooth and glabrous other than lenticels, bark of trunk; initially smooth barked and becomes exfoliating with age.

Foliage description:

*Leaf shape.*—Elliptic.

*Leaf division.*—Simple.

*Leaf aspect.*—Upward to horizontal.

*Leaf base.*—Narrowly cuneate.

*Leaf apex.*—Acute.

*Leaf fragrance.*—None.

*Leaf number.*—Average of 15 per stem 11 cm in length.

*Leaf venation.*—Pinnate, average of 18 per leaf, upper surface 144B in color on midrib and with other veins matching leaf color, lower surface all veins 146D in color.

*Leaf margins.*—Serrate.

*Leaf arrangement.*—Alternate.

*Leaf internode length.*—An average of 7 mm.

*Leaf attachment.*—Petiolate.

*Leaf surface.*—Glabrous and satiny on upper surface and glabrous and dull on lower surface.

*Leaf size.*—Average of 3.2 cm in length and 2.2 cm in width.

*Leaf color.*—Young leaves; 144A on upper surface and lower surface, mature leaves; N137A on upper surface and 147B on lower surface, fall leaves; a blend of 160A, 138C, and 163B on upper and lower surface.

*Petioles.*—An average of 3 mm in length and 1 mm in width, 144B in color, finely pubescent surface.

Flower description:

*Flowers.*—Typical for the species, not present on plants available for data collection.

*Fruit/seed.*—Typical for species, fruit is dry and rounded and flattened in shape, estimated to be 1.5 cm in diameter, forming a broad papery wing encircling the seed, not present on plants available for data collection.

It is claimed:

1. A new and distinct cultivar of *Ulmus* tree named 'DavesStraightUp' as herein illustrated and described.

* * * * *